United States Patent
Shinar et al.

(10) Patent No.: US 6,438,206 B1
(45) Date of Patent: Aug. 20, 2002

(54) CONTINUOUSLY PUMPED MINIATURE X-RAY EMITTING DEVICE AND SYSTEM FOR IN-SITU RADIATION TREATMENT

(75) Inventors: Guy Shinar, Rehovot; Aharon Goldschmidt, Nes Ziona, both of (IL)

(73) Assignee: X-Technologies, Ltd., Orangeburg, NY (US)

( * ) Notice: Subject to any disclaimer, the term of this patent is extended or adjusted under 35 U.S.C. 154(b) by 0 days.

(21) Appl. No.: 09/693,187

(22) Filed: Oct. 20, 2000

(51) Int. Cl.[7] .................................................. A61N 5/00
(52) U.S. Cl. ........................ 378/123; 378/119; 378/122; 600/425
(58) Field of Search ................................ 378/119, 122, 378/123, 121, 136; 600/427, 425

(56) References Cited

U.S. PATENT DOCUMENTS 5,438,605 A * 8/1995 Burke et al. ................ 378/135
6,148,061 A * 11/2000 Shefer et al. ............... 378/121

OTHER PUBLICATIONS

Christensen's Physics of Diagnostic Radiology, Thomas S. Curry, III, M.D., James E. Dowdey, Ph.D., and Robert C. Murray, Jr., Ph.D., Lippincott Williams & Wilkins, 4th edition, Chapter 2, pp. 10–35.*

* cited by examiner

Primary Examiner—David P. Porta
Assistant Examiner—Therese Barber
(74) Attorney, Agent, or Firm—Rossi & Associates (57) ABSTRACT

An apparatus and method for in-situ x-ray radiation treatment utilizes different types of miniature energy transducers to emit x-rays. Each type of energy transducer includes a transducer body, a cathode provided at one end of the transducer body, and an anode provided at another end of the transducer body. The transducer body, cathode and anode define a cavity that communicates with an evacuation opening. A desired vacuum is achieved and maintained by a dynamic pumping mechanism that draws a vacuum in the cavity via the evacuation opening.

24 Claims, 10 Drawing Sheets

CONTINUOUSLY PUMPED MINIATURE X-RAY EMITTING DEVICE AND SYSTEM FOR IN-SITU RADIATION TREATMENT

FIELD OF THE INVENTION

The present invention relates to an apparatus and method for providing x-ray therapy in humans. More specifically, the present invention relates to an apparatus and method for providing in-situ radiation treatment that utilizes a miniature energy transducer to produce x-rays, wherein the energy transducer defines a cavity that communicates with an evacuation opening and is continuously evacuated through a flexible tube by a dynamic pumping mechanism in order to maintain a desired vacuum level.

BACKGROUND OF THE INVENTION

Restenosis is a heart condition that afflicts 35%–50% of all people who undergo balloon angioplasty to improve blood flow in narrowed sclerotic arteries. The condition consists of a significant re-closing of the treated artery segment hours to several months after the procedure. As a result, the arterial lumen size is decreased and the blood flow downstream from the lesion site is impaired. Consequently, patients afflicted with restenosis must undergo an additional balloon angioplasty, and in some cases a coronary bypass surgery must be performed. Aside from the pain and suffering of these patients, recurrent stenosis is also a serious economic burden on society, with estimated expenses as high as 3.0 billion dollars per year in the United States economy alone.

Attempts to treat restenosis have been concentrated in both the pharmacological and medical device areas. While pharmacological solutions have been proven effective in treating only acute restenosis, a condition developing immediately after balloon angioplasty, some progress has been made with medical devices in the treatment of long term restenosis, a condition that develops up to a few months following balloon angioplasty. An example for such medical device is the stent. Stents can be inserted into an occluded artery to hold it open. Stents have been shown to prevent two of the three mechanisms that cause recurrent stenosis, namely, elastic recoil of the artery and negative remodeling of the arterial structure. The third mechanism, neointimal growth, consists of hyper-proliferation of smooth muscle cells from the lesion into the lumen and is not prevented by stents.

Ionizing radiation holds great promise for treating restenosis. Ionizing radiation serves to damage undesirable hyper-proliferating tissue and ultimately to prevent the hyper-proliferation of smooth muscle cells in the irradiated region. Research has shown that gamma and beta radiation delivered at the location of stenotic lesions effectively stop both animal and human intimal proliferation. The effective, yet non-hazardous, required dose to treat human restenosis is between seven and forty Gray (mjoule/gram), preferably a dosage greater than fifteen Gray measured two mm from the center of the radiation source that penetrates the artery wall at a two mm depth over the lesion length.

In view of the above, various methods have been proposed to provide ionizing radiation treatment. For example, radiation catheters, based on the use of radioactive sources such as beta-emitting $^{32}P$, $^{90}Sr/^{90}Y$, $^{188}W/^{188}Re$, beta+ emitting $^{48}V$ or gamma emitting $^{192}Ir$, are at various stages of development and clinical evaluation. The radioactive sources, in a variety of configurations, are introduced to the treatment sites using special radiation catheters and the radioactive source is placed at the treatment site for a predetermined time period as to deliver the proper radiation dose. Radioactive stents are also used as alternative delivery means, incorporating some of the above radioactive isotopes.

The gamma and beta radioactive sources used by the present radiation catheters and radioactive stents, however, have several drawbacks including a limited ability to provide selective control over the dose distribution or overall radiation intensity, and the logistical, regulatory, and procedural difficulties involved in dealing with radioactive materials. In addition, gamma-emitting devices jeopardize patients by exposing healthy organs to dangerous radiation during the introduction of the radiation source. Hospital personnel that handle radioactive materials are also at risk due to exposure. In addition to the risks these devices impose on patients, hospital staff, and the environment, use of these devices invokes a regulatory burden due to the need to comply with nuclear regulatory requirements.

An additional approach to providing ionizing radiation treatment is through the use of an x-ray emitting energy transducer that is not radioactive. Conventional x-ray radiation for radiotherapy is produced by high-energy electrons generated and accelerated in a vacuum to impact a metal target. The emitted x-ray power is directly proportional to the electron beam current. However, the efficiency of x-ray generation is independent of electron current, but rather depends on the atomic number of the target material and on the acceleration voltage. Yet, another method for the production of x-rays is by direct conversion of light into x-ray radiation. It is known that the interaction of light with a target can produce highly energetic x-rays when the power densities achieved are in the range of $10^{16}$–$10^{17}$ watt/cm. With the development of femtosecond laser, such power densities are achievable with moderate size lasers (See C. Tillman et al, NIMS in Phys. Res. A394 (1997), 387–396 and U.S. Pat. No. 5,606,588 issued to Umstadter et al., the contents of each of which are incorporated herein by reference). A 100 femtosecond, one mJ laser pulse focused down to a 3 micron spot, for example, will reach this power density level.

A variety of medical applications of the direct laser light conversion method of xray generation are currently in the development stage. The direct laser light conversion method, for example, has been considered for medical imaging (See, Herrlin K et al. Radiology (USA), vol. 189, no. 1, pp. 65–8, October 1993). Another medical application of femtosecond lasers is in improved non-thermal ablation of neural or eye tissue for surgical purposes (See, F. H. Loesel et al. Appl.Phys.B 66,121–128 (1998)). The development of compact table top models of femtosecond lasers makes laser generated x-rays an attractive alternative for radioactive material based radiotherapy.

Based on the above, an x-ray radiation treatment apparatus and method has been developed. In x-ray treatment an internal x-ray emitting miniature energy transducer generates x-rays in-situ. Co-pending and commonly assigned U.S. patent application Ser. No. 09/325,703 filed Jun. 3, 1999, and U.S. patent application Ser. No. 09/434,958 filed Nov. 5, 1999, describe miniaturized energy transducers that are coupled to flexible insertion devices to permit x-ray radiation treatment within the human body. Use of the miniaturized x-ray emitting energy transducer offers certain advantages with respect to intra vascular gamma and beta sources. These advantages are, but are not limited to, localization of radiation to the treatment site so that the treatment site may be irradiated with minimal damage to surrounding healthy tissue; reduction of hospital personnel risk due to exposure to radioactive materials; and minimization of the regulatory burden and additional costs that arise from the need to comply with nuclear regulatory requirements.

A variety of different types of cathode and anode structures have been proposed for the energy transducer. One proposal is to utilize a hollow cathode, which includes a cathode shell that defines a cavity. A light pulse is introduced into the cavity in order to heat an outer surface of the cathode shell, thereby causing thermionic emission of electrons from the outer surface. Another proposal for a hollow cathode incorporates the use of an electron escape nozzle, wherein an ion and electron plasma is generated in the cavity either by applying a light signal to an inner surface of the cathode shell or by providing a spark gap in the cavity of the conducting cathode shell. The electrons exit the cathode shell via the escape nozzle and are accelerated to the anode upon the application of a voltage pulse to the cathode. Still further, in a linear reverse cathode emission type of transducer, an anode is located at a first end of a transducer body and an emission element is located at a second end of the transducer body opposite the anode. The emission element is either a photoemission electron source or a thermionic emission surface, and generates electrons when activated by a light source. Furthermore, in a distally illuminated plasma cathode an anode is located at the first end of a transducer body and a cathode is located at a second end of a transducer body opposite to the anode. An ion and electron plasma is generated by applying a light pulse to the surface of the cathode. Electrons are extracted from the plasma by the application of a high voltage pulse to the anode. They are accelerated by the said high voltage pulse and strike the anode, where x-rays are produced.

Co-pending and commonly assigned U.S. patent application Ser. No. 09/504,709, filed Feb. 16, 2000, the contents of which are incorporated herein by reference, describes an explosive electron emission plasma cathode structure wherein one of the preferred embodiments utilizes liquid metal such as gallium-indium. The liquid metal is deposited inside a hollow, needle shaped, conducting cathode, which is made, for example, out of tungsten. A pre-pulse of voltage, typically 1–10 kV in magnitude, is applied to the cathode for duration of less than 100 microseconds. As a result, the surface of the liquid metal obtains the shape of a sharp tip having a typical diameter of 1–20 microns. A second pulse is then applied, typically of 10–100 kV, for duration of 1–100 nanoseconds. As a result, plasma is formed at the liquid metal tip. The high voltage pulse extracts electrons out of the plasma and accelerates them towards the anode. At the anode, the electrons' kinetic energy is converted to x-ray photons and heat. Further still, in another preferred embodiment of said plasma cathode, the cathode may be an explosive electron emission cathode that contains a single carbon fiber or a bundle of carbon fibers. A high voltage pulse, of typical magnitude of 10–100 kV and typical duration of 1–100 nanoseconds, is applied to the cathode. As a result, part of the carbon fiber, or fibers' tips is sublimated and plasma is formed. The high voltage pulse extracts electrons out of the plasma. These electrons are accelerated by the high voltage pulse towards the anode. At the anode, the electrons' kinetic energy is converted to x-ray photons and heat.

Regardless of the type of anode and cathode structure utilized, an appropriate level of vacuum must be maintained within the transducer body. A vacuum is required to permit the production of electrons at the cathode, to enable uninterrupted acceleration of electrons from the cathode to the anode over a voltage difference that can typically vary from 10 kV to 100 kV, and to prevent high voltage breakdown within the transducer body, as breakdown probability is enhanced by ionization of the molecules of any residual gases present within the transducer body. The required vacuum level depends mainly on the electron production mechanism that is employed in the device. This level can vary from $10^{-10}$ Torr for x-ray emitters utilizing surface based electron emission mechanisms such as photo-emission or field emission, down to $10^{-2}$ Torr or less for x-ray emitters employing pulsed plasma based mechanisms.

One of the major challenges in designing miniature x-ray transducers for in-situ use is maintaining the required vacuum level inside the transducer. The vacuum may be degraded due to several processes. Out-gassing from the electrodes and the insulating tube into the evacuated space is a major potential source of vacuum degradation. Other reasons for vacuum degradation include leaking of gases from outside the insulating tube through the walls of the insulating tube and seals and desorption of gases from the electrodes throughout the operation of the transducer.

The evacuated volume is about 10 mm$^3$ as the transducer body is preferably several millimeters in length and about 1–2 mm in diameter. If a typical leak rate of gas into the cavity is $10^{-11}$ Torr-liter/sec, the pressure inside the cavity will rise at a rate of approximately 0.1 Torr/day. Unless a mechanism exists to absorb the entrant gases, the vacuum level will be quickly degraded to a point where x-ray emission is not possible. The above-mentioned analysis also applies to desorption of gases during the operation of the energy transducer. The surface area defining a cavity within the transducer body is about 30 mm$^2$. Thus, the ratio of surface area to volume is approximately 3 mm$^{-1}$. The length and diameter of conventional x-ray tubes sized for most medical applications are about 100 times larger than the miniaturized energy transducer being considered, and conversely, the surface to volume ratio is 100 times smaller than that of the miniaturized energy transducer. As out-gassing is a major potential source-of vacuum degradation, the above mentioned comparison implies that for any given surface specific out-gassing rate the vacuum will be degraded 100 times faster in a miniaturized energy transducer than in a conventional x-ray tube. Thus, enhancing vacuum preservation before and throughout the operation of an x-ray emitting miniaturized energy transducer is particularly crucial.

In order to maintain the required vacuum level, getter material may be introduced through one or more components to the miniature x-ray transducer prior to final assembly thereof. Getter material is preferably made of titanium, zirconium, tantalum, iron, vanadium, aluminum or an alloy composed of two or more of these materials. Suitable types of getters for this application are, for example, non-evaporable sintered porous type getters such as ST701, ST702 and ST707 getter alloys, manufactured by SAES-getters, Milan, Italy. The getter material is activated by heating the miniature x-ray transducer to a temperature that is preferably 300° C. or more. This heating step may be a by-product of the routine bake-out processes necessary to out-gas the x-ray emitting transducer before it is sealed off or can be performed as a separate manufacturing step. During the above mentioned heat activation process, the native oxide on the getter material surface is decomposed and oxygen diff-uses into the bulk of the getter material, exposing a fresh, ultra-clean surface of getter material. The resultant surface of the getter material has beneficial absorption characteristics, and can typically absorb gases, for example $H_2$, CO, and $H_2O$ vapor. However, the getter material cannot absorb non-reactive gases such as all the noble gases and highly stable compounds such as Methane. Thus, the vacuum degradation problem is not eliminated completely by the use of getter material. This is represented by the following numerical example.

EXAMPLE

The following conditions are assumed: The electron production mechanism, which is employed within the miniature x-ray transducer, is such that the allowable operating pressure in the transducer is $10^{-4}$ Torr. The required evacuated volume is 10 mm$^3$ =$10^{-5}$ Liter. The lowest detectable leak rate of air with state of the art technology is $10^{-13}$ Torr-Liter/sec. The fraction of non-absorbable gases in air is 1%. The example intends to show the pressure rise within a miniature x-ray transducer with an expected shelf life of 100 days ~$10^7$ sec. It is assumed that the pressure rise is due to leaking of non-absorbable gases alone.
Therefore, this pressure rise is:

($10^{-13}$ Torr-Liter/sec*1%*100 days)/$10^{-5}$ Liter =$10^{-3}$ Torr

This result, $10^{-3}$ Torr, is an order of magnitude above the maximum allowable pressure inside the transducer.

In addition, the space within the x-ray emitting transducer that is occupied by the getter material should be taken in consideration. This space is particularly limited inside miniature x-ray transducers intended for use inside the human body.

In view of the above, it is an object of the present invention to provide a mechanism for preserving the vacuum level in miniaturized energy transducers that emit x-rays, which removes stray gases regardless of their chemical reactivity, thus overcoming the problem of vacuum degradation due to non-absorbable gases.

It is another object of the present invention to provide a simple, inexpensive method to maintain vacuum level within a miniature x-ray emitter that does not require neither the introduction of getter material nor vacuum sealing prior to the assembly of the x-ray emitter.

Another object of the present invention to provide a device for in-situ x-ray radiation treatment that is easy to handle due to lack of vacuum sealed components and with relatively long shelf life due to the lack of need to maintain an appropriate vacuum level during the operation of the device alone.

SUMMARY OF THE INVENTION

The present invention provides a device and method for in-situ x-ray radiation treatment in humans, wherein different types of miniature energy transducers are utilized to emit x-rays. More specifically, an x-ray emitting energy transducer is provided that includes a transducer body having a first end and a second end, a cathode provided at the first end of the transducer body; and an anode provided at the second end of the transducer body. The transducer body, cathode, and anode define a cavity that communicates with an evacuation opening. A desired vacuum level is maintained within the cavity by evacuating the cavity through the evacuation opening with a dynamic pumping mechanism. The evacuation opening preferably extends through at least one of the anode, the cathode, and the transducer body.

An elongated flexible insertion device is also provided that includes an electrically conductive inner core, a dielectric material that surrounds the inner core, an outer shield that surrounds the dielectric material, an outer layer of electrical insulation that surrounds the outer shield; and a pumping conduit. In a preferred embodiment, the inner core is a hollow conduit that defines the pumping conduit. In another embodiment, the pumping conduit is embedded within the dielectric material. In a still further embodiment, the pumping conduit is coupled to the exterior of the outer layer of electrical insulation. Alternatively, the pumping conduit is embedded within the outer layer of electrical insulation.

The x-ray emitting energy transducer and flexible insertion device are coupled to an external unit that includes a power supply, a vacuum pump, a control unit and may optionally include a light source. In operation, the miniature x-ray energy transducer is positioned at a treatment site, evacuation of the miniature x-ray transducer is achieved to a desired vacuum level; and the miniature x-ray energy transducer is energized to achieve a predetermined radiation dosage. Stray gas molecules, that are either created during the operation of the miniature x-ray energy transducer or which diffuse into the transducer due to out gassing or leaks, are continuously evacuated during the operation of the miniature xray energy transducer in order to maintain the desired vacuum level. A dosimetry may optionally be provided to monitor the radiation dosage.

Other advantages and features of the invention will become apparent from the following detailed description of the preferred embodiments and the accompanying drawings.

BRIEF DESCRIPTION OF THE DRAWINGS

The invention will now be described with reference to certain preferred embodiments thereof and the accompanying drawings, wherein.

DETAILED DESCRIPTION OF THE PREFERRED EMBODIMENTS

The present invention is particularly applicable to a system for the delivery of x-ray radiation to localized targets inside and outside the human body. Some therapeutic uses for the invention include the irradiation of coronary lesions to prevent restenosis and the treatment of tumors and of arterio-venous malformations. It will be understood, however, that the invention is not limited to these particular applications.

Figure 1:
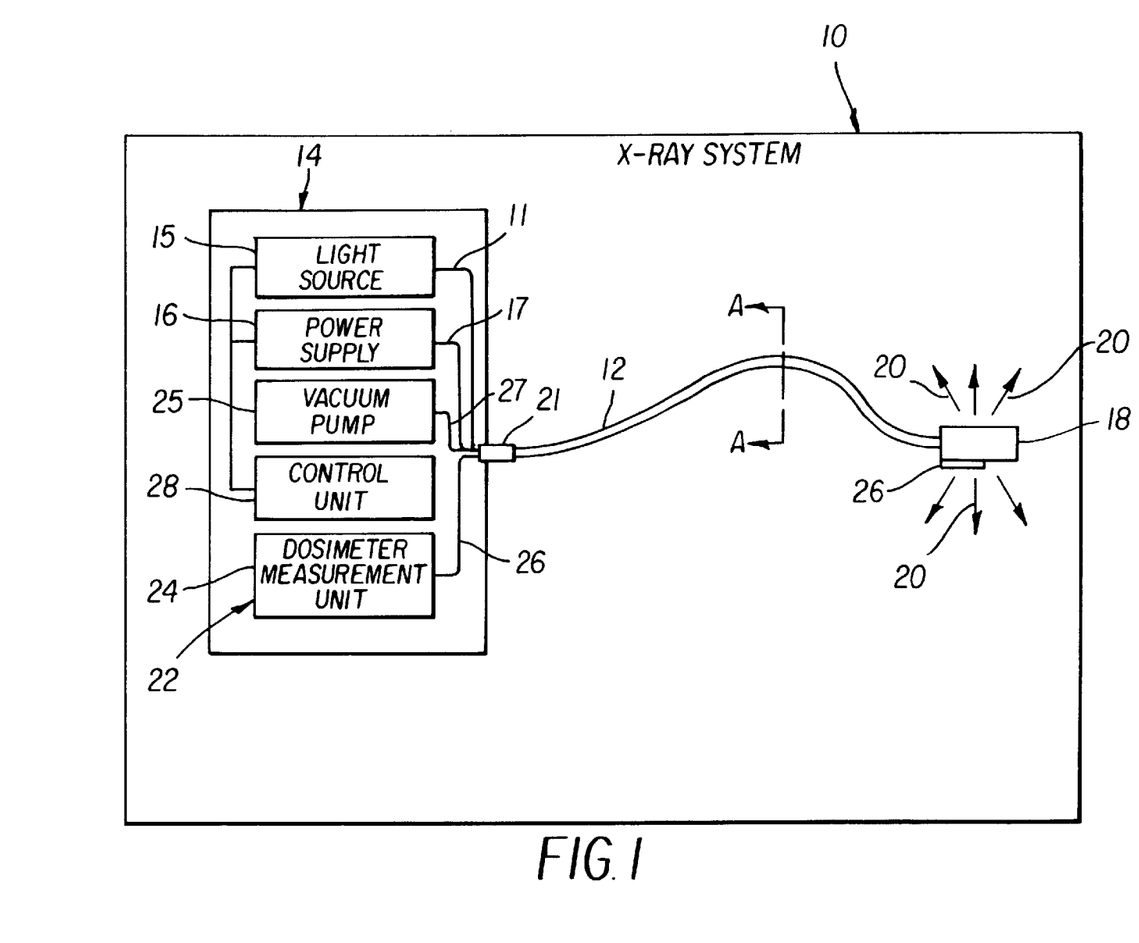
FIG. 1 is a functional block diagram of an x-ray radiation treatment system in accordance with the present invention.

FIG. 1 illustrates an x-ray system 10 in accordance with the present invention. The system 10 includes a miniature energy transducer 18 that is coupled to a distal end of a flexible insertion device 12. The flexible insertion device 12 delivers energy from an external unit 14 to the miniature energy transducer 18, which preferably converts electrical and/or optical signals received from the external unit 14 into x-ray radiation and distributes the x-ray photons (illustrated by arrows 20) in a predetermined distribution pattern. The miniature energy transducer 18 is evacuated through the flexible insertion device 12, with its proximal end connected to a vacuum pump 25 that is preferably housed within the external unit 14. The vacuum pump 25 is preferably a Turbo vacuum pump, such as a Varian V-70, manufactured by Varian Vacuum Products, Lexington, Mass. While the external unit 14 is located outside the patient's body, the flexible insertion device 12 is manipulated to place the miniature energy transducer 18 in an area to be treated within the patient's body.

The miniature energy transducer 18 is preferably surrounded by x-ray transmissive insulation 19 (illustrated in FIG. 8–FIG. 13) that can be presented in direct contact with the human body. The transmissive insulation 19 may be a material coated on an outer surface of the miniature energy transducer 18. Alternatively, the transmissive insulation may take the form of a capsule that encapsulates the miniature energy transducer 18. In any case, the miniature energy transducer 18 is preferably a relatively low-cost, replaceable and disposable unit. This avoids the necessity of complex sterilization processes required for instruments that are intended for multiple uses.

The system 10 may further contain a dosimetery system 22, comprised of a dosimeter measurement unit 24 connected to a scintillating optical fiber 26. Preferably, the scintillating optical fiber 26 is a standard plastic scintillating optical fiber, containing embedded dopant atoms that produce light photons upon being irradiated with x-ray photons. The distal end of the scintillating optical fiber 26 is located in the immediate vicinity of the miniaturized energy transducer 18. Preferably, the bulk of the length of the scintillating optical fiber 26 is housed within the flexible insertion device 12. The dosimeter measurement unit 24 is preferably housed within the external unit 14, and it is connected to a control unit 28, which is also housed within the external unit 14.

In general, the external unit 14 is adapted to provide electrical and/or optical signals through the flexible insertion device 12 that is correspondingly configured to deliver the energy to the miniature energy transducer 18. Accordingly, the external unit 14 is provided with a power supply 16, such as a voltage generator respectively connected through an electrical conductor 17, preferably a coaxial cable, to the miniature energy transducer 18. In another preferred embodiment, the external unit 14 may be provided with a light source 15, for example a laser that is respectively connected through an optical conductor 11 to the miniature energy transducer 18. The vacuum pump 25 evacuates stray gas molecules from the miniature energy transducer 18 through a pumping tube 27, preferably incorporated within the flexible insertion device 12. The proximal end of the flexible insertion device 12 is connected to the external unit 14 through a connector 21, which provides a leak-tight mechanical connection of the proximal end of pumping tube 27 to the vacuum pump 25, as well as an electrical connection of the electrical conductor 17 to the power supply 16 and the connection of the optical conductor 11 to the light source 15. The distal end of pumping tube 27 is connected to the proximal end of miniature energy transducer 18 in a leak-tight connection.

The control unit 28 directs the power supply 16 and the light source 15 to deliver electrical and/or optical signals through the flexible insertion device 12 to the miniature energy transducer 18 as required by the operator. During x-ray treatment, the control unit 28 may also receive information from the dosimeter measurement unit 24 and may use this information to achieve the required dosage amount of radiation, providing the system with a feedback mechanism. Thus, the duration and amplitude of the energy supplied by the power supply 16 and/or by the light source 15, as well as the total treatment time, may be varied to control the distribution of the x-ray radiation produced by the miniature energy transducer 18.

Figure 3:
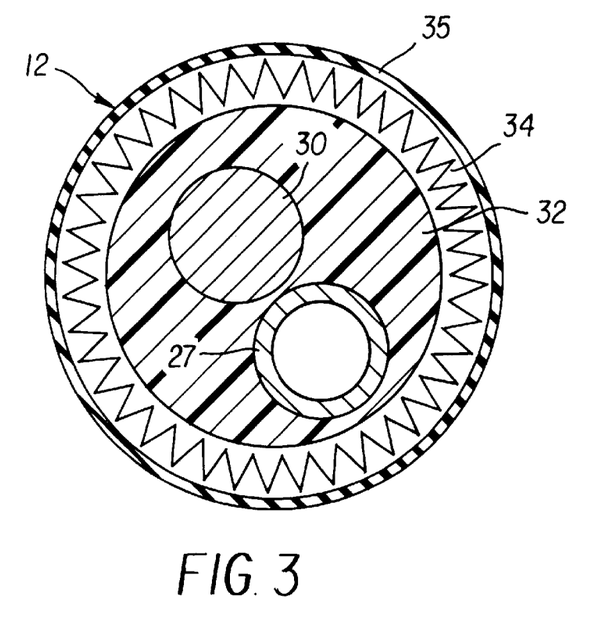
Figure 4:
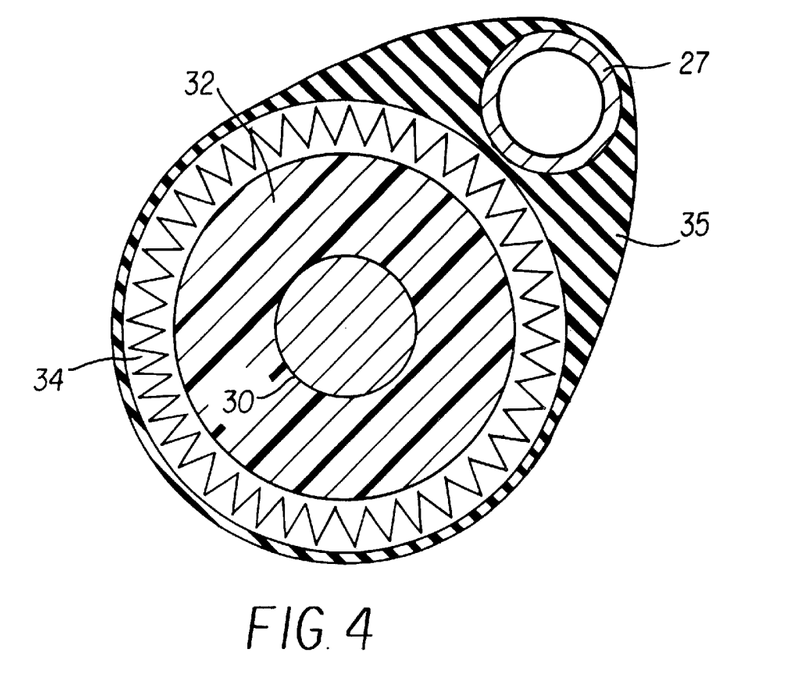
Figure 5:
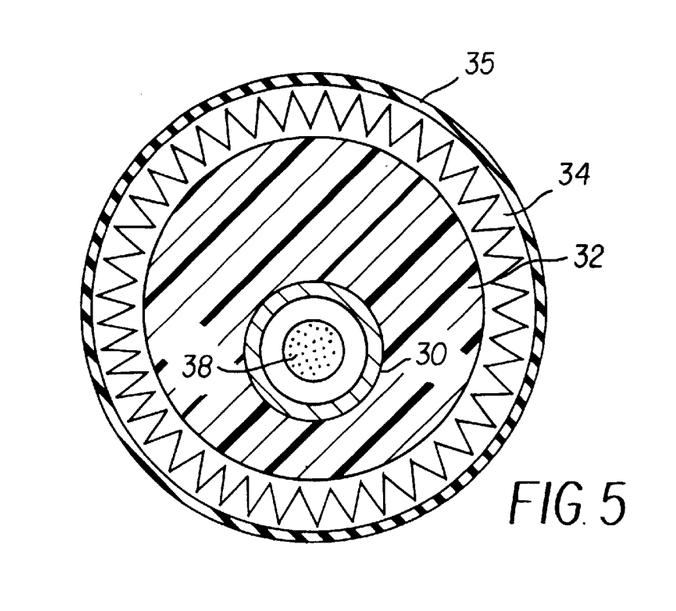
Figure 6:
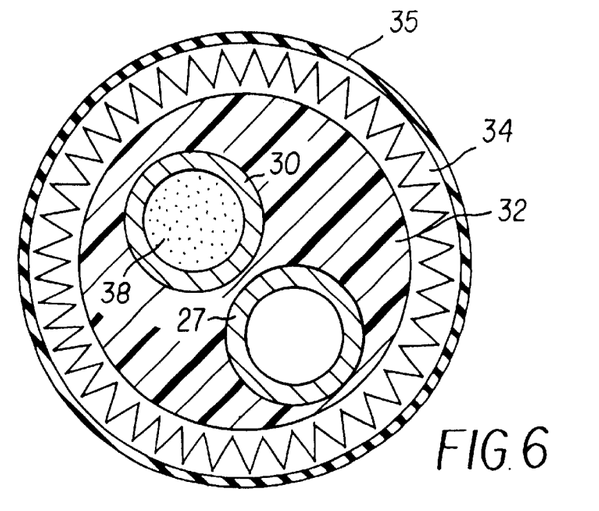
Figure 7:
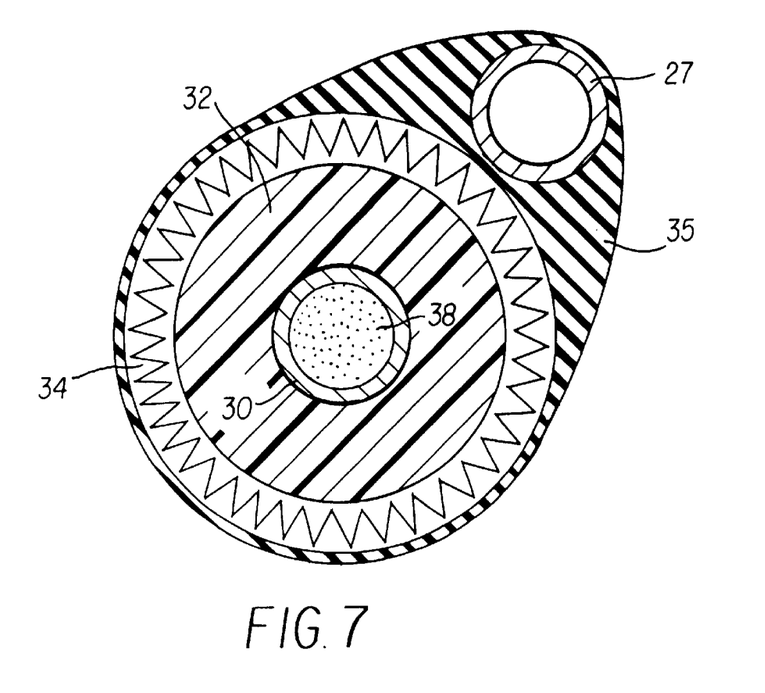

FIGS. 2–7 show cross-sections of several preferred embodiments of the flexible insertion device 12 taken along line A—A of FIG. 1. The flexible insertion device 12 preferably combines electrical conductor 17, pumping tube 27 and the optical conductor 11 into one structure, thus economizing the catheter diameter that must be preferably 1.7 mm or less, for coronary applications, and thereby allowing the flexible insertion device 12 to follow the contours of a blood vessel or any other body cavity. The flexible insertion device 12 is preferably a coaxial cable that is comprised of a core 30, a dielectric 32, a shield 34, and an outer layer of electrical insulation 35. The shield 34 is preferably a uniformly coated shield, a uniform foil shield, or a braided conducting shield. The core 30 of the embodiment illustrated in FIG. 2 serves both as an electrical conductive element and as a pumping tube. Thus, core 30 is a hollow tube, which can be made of any conductive material with out-gassing rate low enough to enable effective pumping of miniature energy transducer 18. For example pumping tube 27 is made of a metal alloy such as Nitinol. The optical conductor 11, preferably an optical fiber 38, may be disposed within the core 30 of this embodiment as shown in FIG. 5. In another embodiment, illustrated in FIG. 3, pumping tube 27 is embedded within the dielectric 32 and runs parallel to core 30 for the entire length of flexible insertion device 12. In another embodiment, illustrated in FIG. 4, the pumping tube 27 may be either embedded within the outer layer of electrical insulation 35 or attached to flexible insertion device 12. The pumping tube 27 in both embodiments illustrated in FIG. 3 and FIG. 4 may be made of any material with an out-gassing rate that is low enough to enable effective pumping of the miniature energy transducer 18. The optical fiber 38 may be part of the core 30 of these embodiments as illustrated in FIG. 6 and FIG. 7.

FIGS. 8–13 illustrate several preferred embodiments wherein the dynamic pumping system is implemented and specifically show preferred modes of connection between the pumping tube 27 and the miniature energy transducer 18. These embodiments utilize various configurations of conducting tubes on which the anode and the cathode of said transducer are installed. Conducting tubes are mainly used within the energy transducers in accordance with this invention as a relatively simple method for joining the electrode components to an insulating tube in a manner that will provide a vacuum-tight seal to the xray generation mechanism. The above-referenced figures describe the preferred embodiments with respect to a generic vacuum-tight structure that provides the mechanical housing for the x-ray production mechanism. However, those skilled in the art will readily recognize various modifications and changes that may be made to the illustrated embodiments, such as using other conducting and insulating materials for the construction of the vacuum-tight structure and other modes of joining the conducting trunks to an insulating tube, without departing from the spirit and scope of the present invention.

Figure 8:
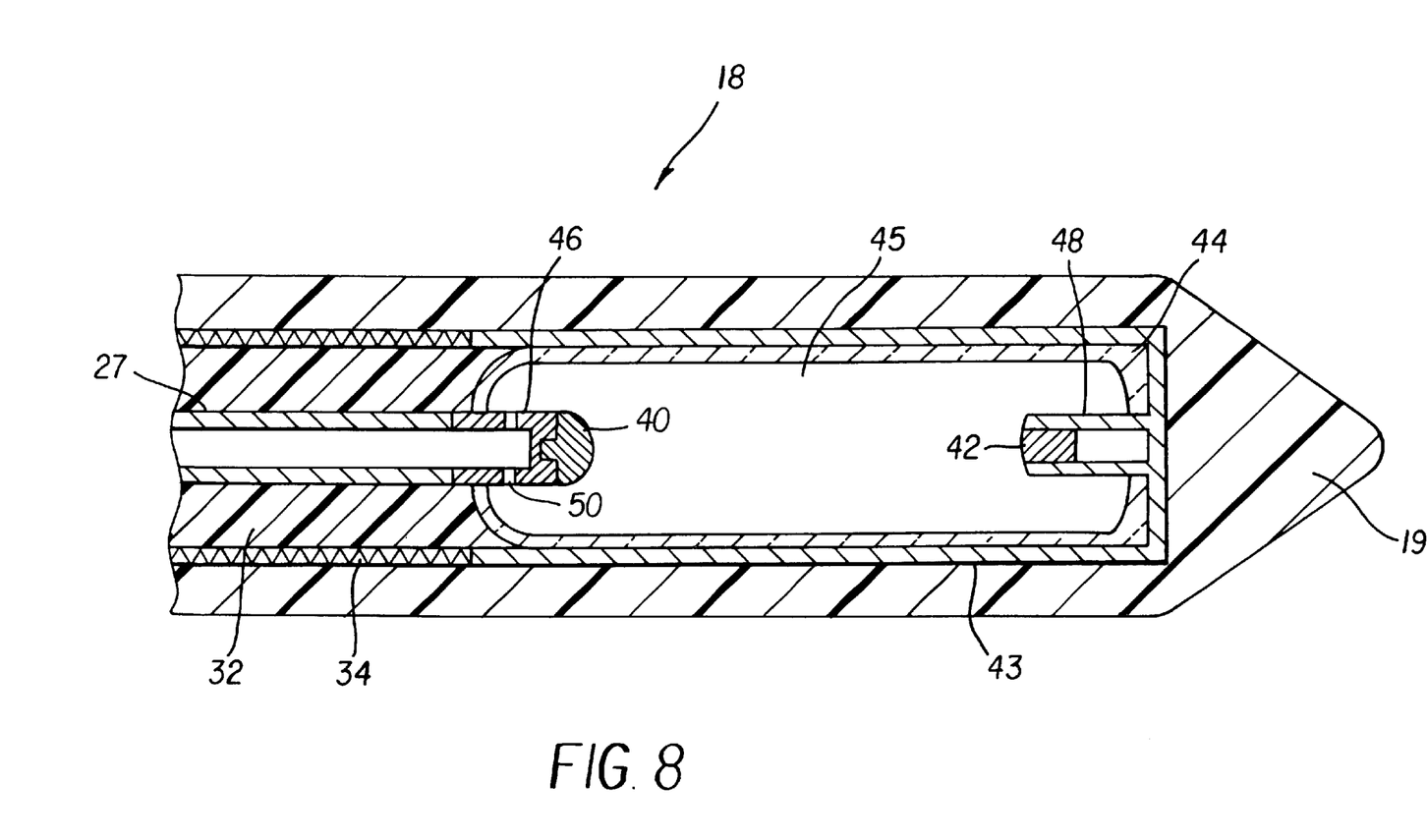
FIG. 8 is a cross-sectional view of an energy transducer in accordance with the invention wherein a pumping tube is connected to a proximal conductive tube.

FIG. 8 describes a preferred embodiment of the energy transducer 18 wherein the conducting anode 40 and the conducting cathode 42 are disposed within a vacuum-tight structure 45. The conducting anode 40 is installed at the distal end of an anode tube 46 that is preferably made from a low expansion glass sealing metal or metal alloy, such as KOVAR, an alloy including approximately 53% iron, 30% nickel and 17% cobalt, manufactured by Goodfellow Cambridge, Ltd. of the United Kingdom. The conducting cathode 42 is installed at the edge of a cathode tube 48, and it is also preferably made from KOVAR.

The attachment of the anode 40 to the anode tube 46 and of the cathode 42 to the cathode tube 48 is achieved by several methods, including mechanical pressure, welding, soldering or brazing. A glass bead (not shown) that is coupled to the anode tube 46 in a vacuum-tight joint, preferably, for example, by baking in reducing atmosphere, is joined to one edge of a glass tube 44, creating a vacuum-tight seal between the anode tube 46 and the glass tube 44, such that a predetermined length of the anode tube 46 remains within the glass tube 44, while the rest of the length of anode tube 46 remains outside glass tube 44. Similarly, another glass bead (not shown) is joined to the other edge of the glass tube 44, creating a vacuum-tight seal between the cathode tube 48 and the glass tube 44 thereby leaving a portion of the cathode tube 48 within the glass tube 44 and the other portion of the cathode tube 48 outside glass tube 44.

Figure 9:
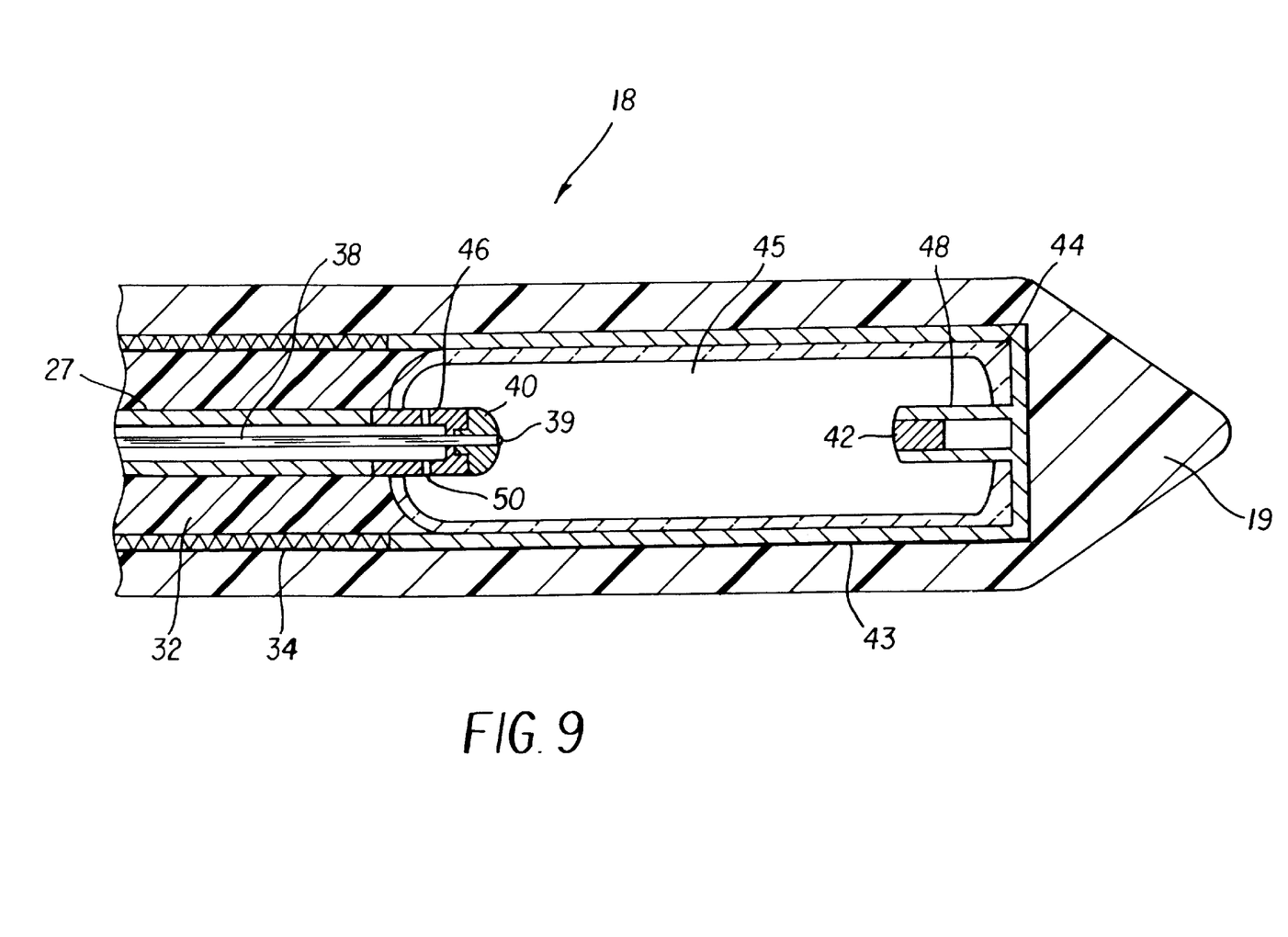
FIG. 9 is a cross-sectional view of an energy transducer in accordance with the invention wherein a pumping tube that is connected to a proximal conductive tube further houses an optical fiber.

The anode tube 46 contains one or more evacuation openings 50, located within the portion of said tube 46 disposed within the glass tube 44. The distal edge of the pumping tube 27 is coupled to the proximal edge of anode tube 46 in a leak-tight connection. The attachment of pumping tube 27 to the anode tube 46 is achieved by several preferred methods including, for example, welding and brazing. In accordance with another preferred embodiment, the pumping tube 27 may further house the optical fiber 38 as illustrated in FIG. 9. The proximal end of optical fiber 38 is connected to light source 15, that is preferably a laser. The distal end of the optical fiber 38 is disposed within the anode tube 46 and the conducting anode 40. A lens 39 may optionally be provided at the end of the optical fiber 38 to focus the laser light. The lens 39 may constitute a separate element or the end of the optical fiber 38 can be shaped in the form of a lens.

Figure 2:
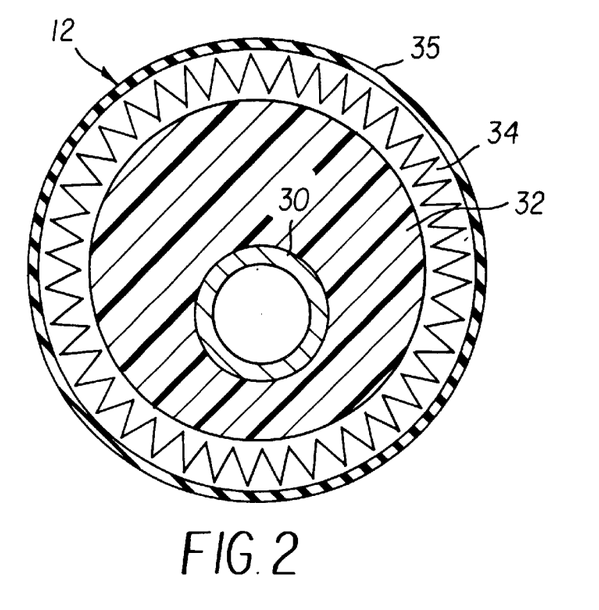
FIGS. 2–7 are cross-sectional views of flexible insertion devices taken along line A—A in accordance with several preferred embodiments of the present invention.

The cross-section of flexible insertion device 12 configured in accordance with embodiments described in FIG. 8 and FIG. 9 is shown in FIG. 2 and FIG. 5 respectively.

Figure 10:
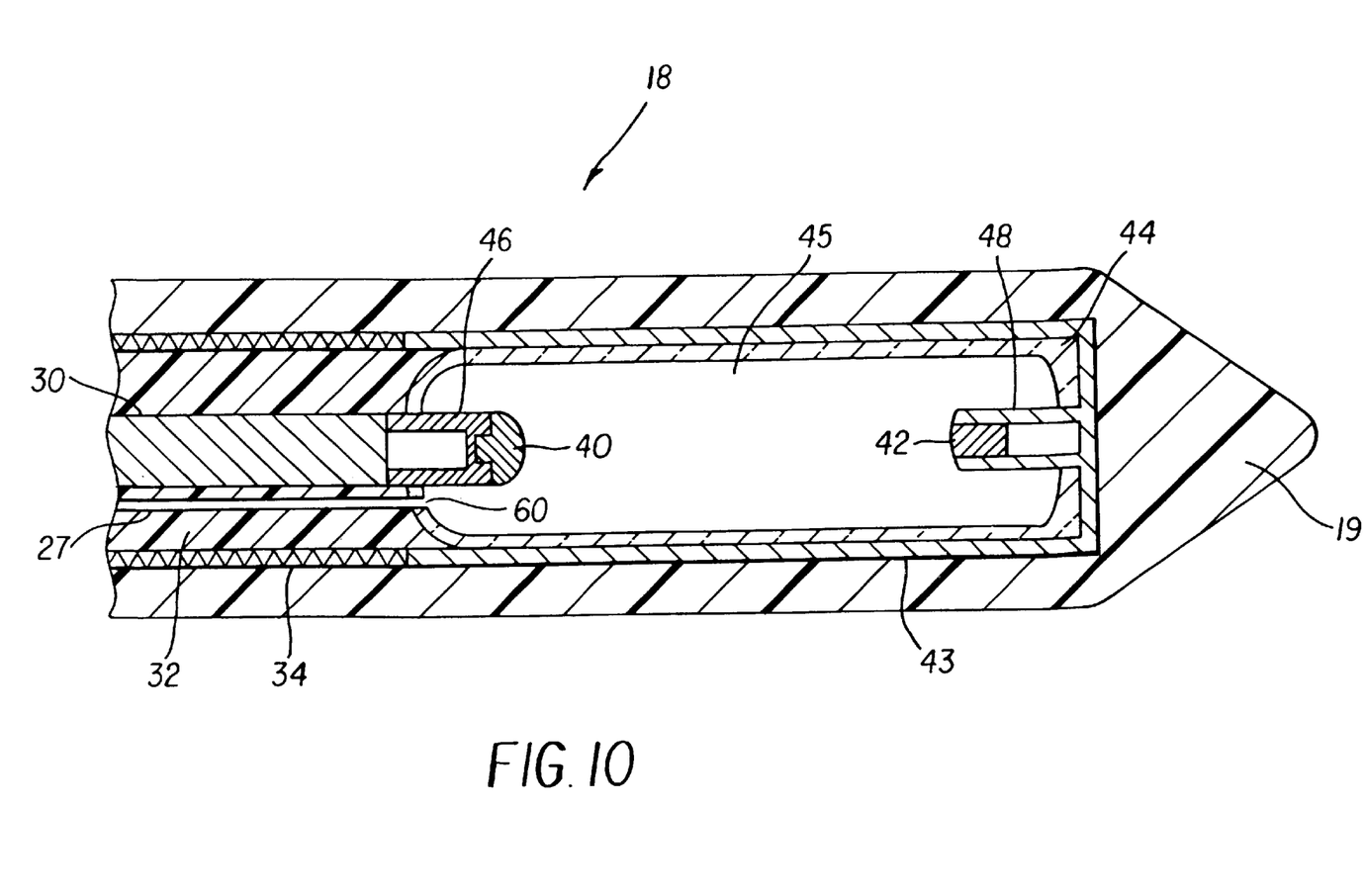
FIG. 10 is a cross-sectional view of an energy transducer in accordance with the invention wherein a pumping tube opens into the energy transducer.

FIG. 10 describes another preferred embodiment of the energy transducer 18 wherein the conducting anode 40 and the conducting cathode 42 are disposed within a vacuum-tight structure 45. The conducting anode 40 is installed at the distal end of an anode tube 46. A glass bead (not shown) that is coupled to the anode tube 46 in a vacuum-tight joint, preferably by baking in reducing atmosphere, is joined to one edge of a glass tube 44, creating a vacuum-tight seal between the anode tube 46 and the glass tube 44, such that a predetermined length of the anode tube 46 remains within the glass tube 44, while the rest of the length of anode tube 46 remains outside glass tube 44. Similarly, another glass bead (not shown) is joined to the other edge of the glass tube 44, creating a vacuum-tight seal between the cathode tube 48 and the glass tube 44 thereby leaving a portion of the cathode tube 48 within the glass tube 44 and the other portion of the cathode tube 48 outside of the glass tube 44. The pumping tube 27 that is embedded within the dielectric 32, runs parallel to the core 30 and opens into the proximal end of miniature energy transducer 18 through an aperture 60 within the glass tube 44. The distal edge of pumping tube 27 is coupled to the glass tube 44 in a leak-tight connection. In accordance with another preferred embodiment illustrated in FIG. 11, the core 30, that provides the electrical connection to the conducting anode 40, may further incorporate the optical fiber 38. The proximal end of optical fiber 38 is connected to light source 15, which may be a laser. The distal end of the optical fiber 38 extends from the distal end of core 30 into the anode tube 46 and the conducting anode 40. A lens 39 may optionally be provided at the end of the optical fiber 38 to focus the laser light. The lens 39 may constitute a separate element or the end of the optical fiber 38 can be shaped in the form of a lens.

Figure 11:
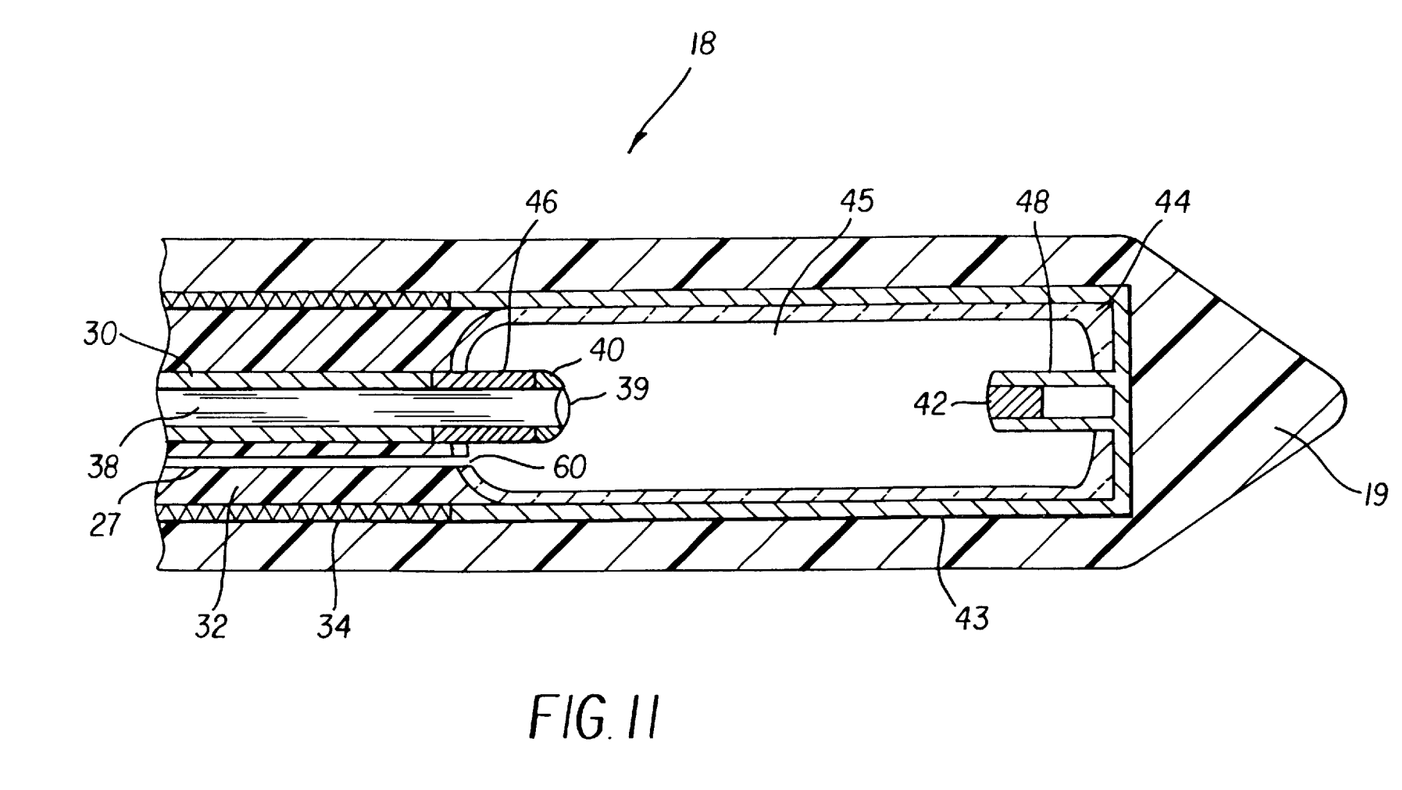
FIG. 11 is a cross-sectional view of an energy transducer in accordance with the invention wherein a pumping tube opens into the energy transducer and the core of the electrical conductor incorporates an optical fiber.

The cross-section of flexible insertion device 12 configured in accordance with embodiments described in FIG. 10 and FIG. 11 is shown in FIG. 3 and FIG. 6 respectively.

Figure 12:
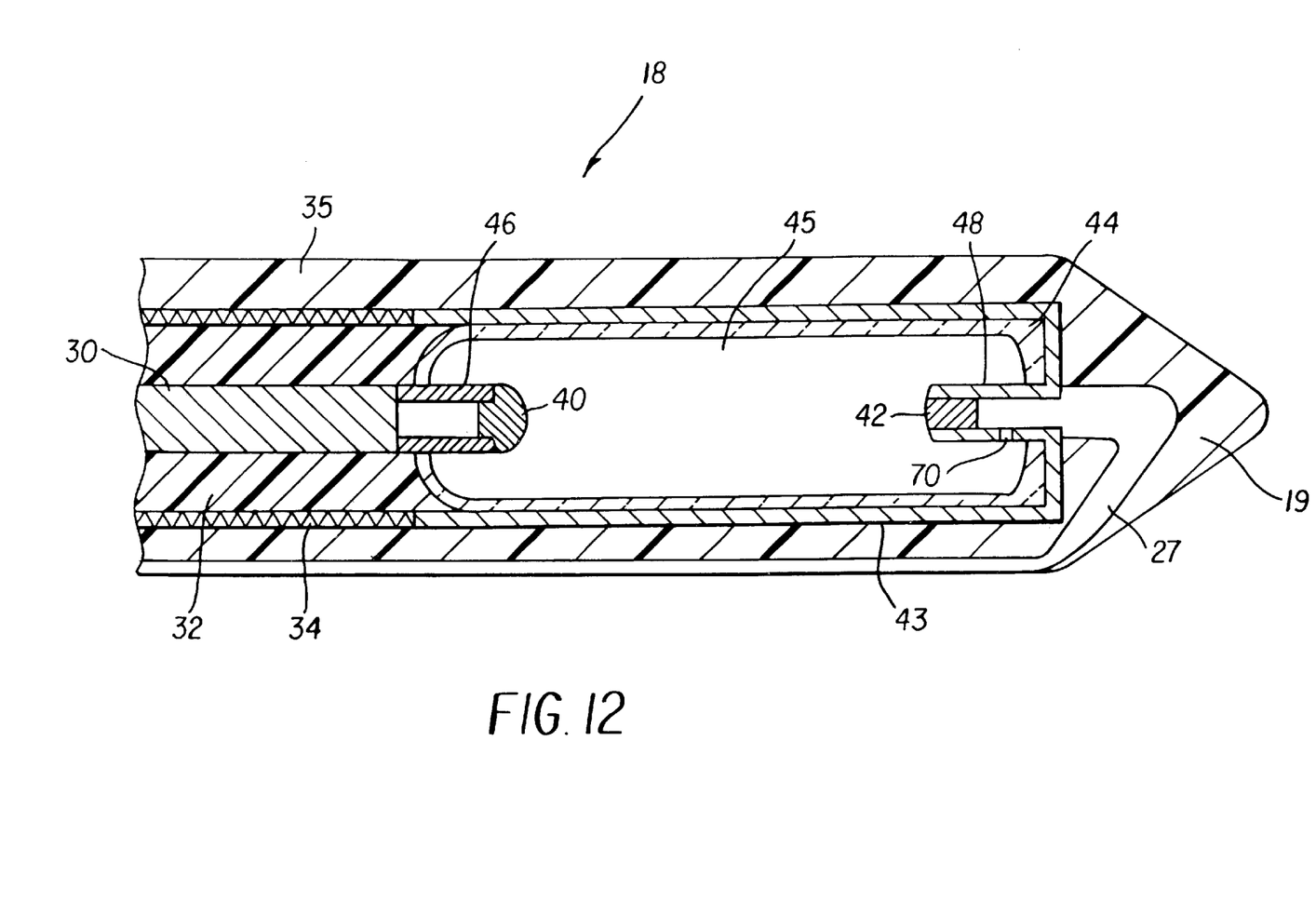
FIG. 12 is a cross-sectional view of an energy transducer in accordance with the invention wherein a pumping tube is connected to a conductive distal tube.

Referring now to FIG. 12, another preferred embodiment of the energy transducer 18 in accordance with the present invention is described, wherein the conducting anode 40 and the conducting cathode 42 are disposed within a vacuum-tight structure 45. The conducting anode 40 is installed at the distal end of an anode tube 46. A glass bead (not shown) that is coupled to the anode tube 46 in a vacuum-tight joint, for example, by baking in a reducing atmosphere, is joined to one edge of a glass tube 44, creating a vacuum-tight seal between the anode tube 46 and the glass tube 44, such that a predetermined length of the anode tube 46 remains within the glass tube 44, while the rest of the length of anode tube 46 remains outside glass tube 44. Similarly, another glass bead (not shown) is joined to the other edge of the glass tube 44, creating a vacuum-tight seal between the cathode tube 48 and the glass tube 44 thereby leaving a portion of the cathode tube 48 within the glass tube 44 and the other portion of the cathode tube 48 outside glass tube 44.

Figure 13:
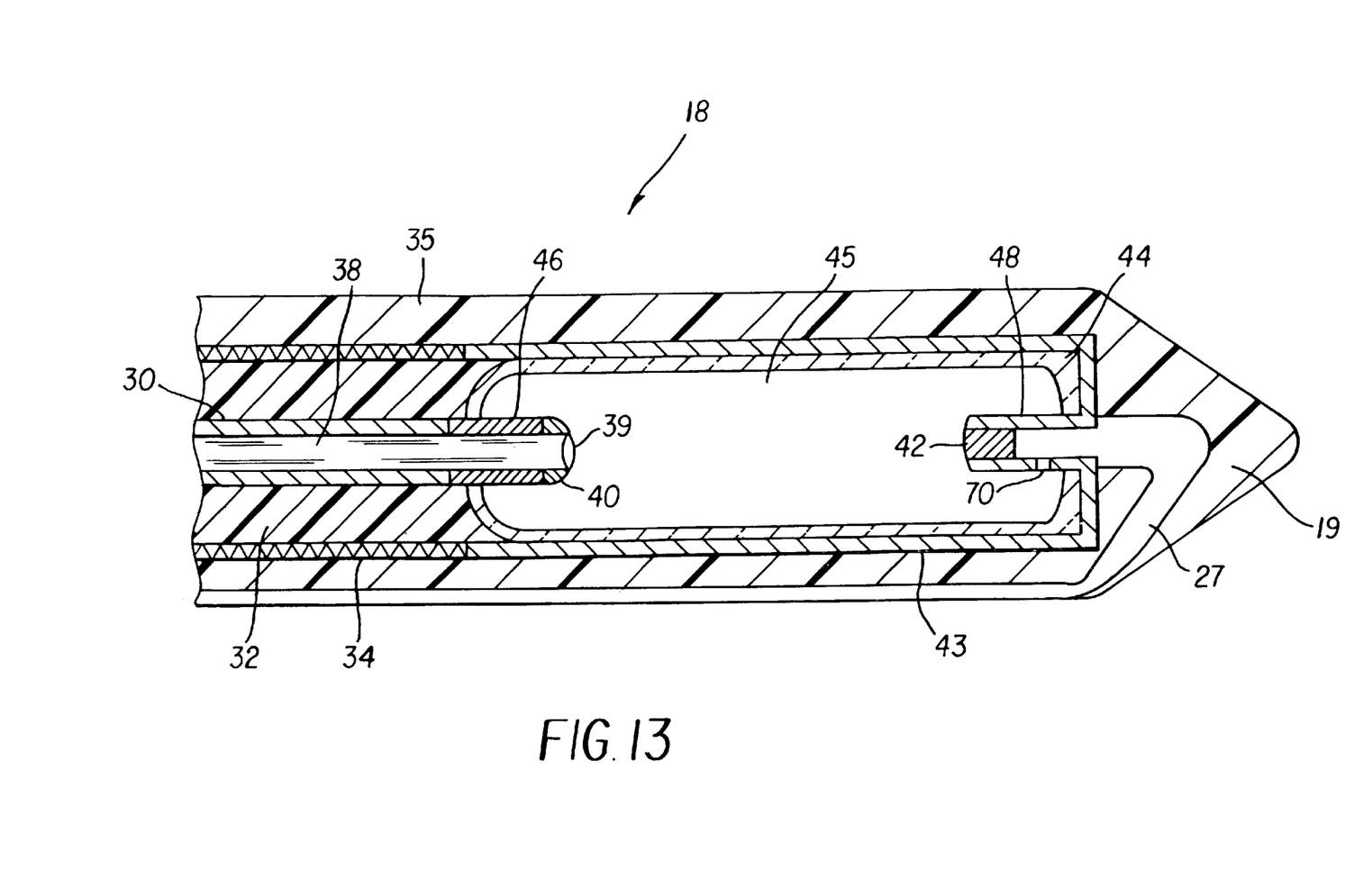
FIG. 13 is a cross-sectional view of an energy transducer in accordance with the invention wherein a pumping tube is connected to a conductive distal tube and the core of the electrical conductor incorporates an optical fiber.

The cathode tube 48 contains one or more evacuation openings 70, located within the portion of said tube 48 disposed within the glass tube 44. The pumping tube 27 is either embedded within the outer layer of electrical insulation 35 and the transmissive insulation 19, both preferably made from the same material and formed as one integral structure, or attached to flexible insertion device 12 and to said transmissive insulation 19. The distal edge of said tube 27 penetrates the transmissive insulation 19 and an outer conductive layer 43, designed to provide an electrical connection to the conducting cathode 42, at the distal end of the energy transducer 18 and joins the distal edge of cathode tube 48 in a leak-tight connection. The attachment of pumping tube 27 to the cathode tube 48 may be achieved by several methods including, for example, welding and brazing. The core 30, that provides the electrical connection to the conducting anode 40, may further incorporate the optical fiber 38 as illustrated in FIG. 13. The proximal end of optical fiber 38 is connected to light source 15, which may be a laser. The distal end of the optical fiber 38 extends from the distal end of core 30 into the anode tube 46 and the conducting anode 40. A lens 39 may optionally be provided at the end of the optical fiber 38 to focus the laser light. The lens 39 may constitute a separate element or the end of the optical fiber 38 can be shaped in the form of a lens.

The cross-section of flexible insertion device 12 configured in accordance with the embodiments described in FIG. 12 and FIG. 13 is shown in FIG. 4 and FIG. 7 respectively.

The operation of the dynamic pumping system will now be described. The structure 45 is evacuated by connecting the proximal edge of pumping tube 27 to vacuum pump 25 through connector 21. During the operation of the preferred embodiments illustrated in FIGS. 8 and 9, stray gas molecules, that are either created during the operation of the energy transducer 18 or diffuse into said vacuum-tight structure 45 due to out gassing or leaks, are pumped out, either through the openings 50 and the pumping tube 27 or through the openings 50 and the gap between the walls of pumping tube 27 and the optical fiber 38, concurrently with the operation of miniature energy transducer 18. In accordance with the operation of the preferred embodiments illustrated in FIGS. 10 and 11, stray gas molecules are pumped out directly through pumping tube 27 concurrently with the operation of miniature energy transducer 18. In accordance with the operation of the preferred embodiments illustrated in FIGS. 12 and 13, stray gas molecules are pumped out through the openings 70 and the pumping tube 27 concurrently with the operation of miniature energy transducer 18.

EXAMPLE

In this example the basic operating parameters of the system are calculated in order to demonstrate the feasibility of the dynamic pumping concept. The following conditions are assumed:

The length of the pumping tube is L=400 cm.
The internal diameter of the pumping tube is D=0.05 cm.
Therefore, the internal surface area of the pumping tube is:

$$A = \pi * D * L = 63 \text{ cm}^2$$

The conductance of the pumping tube is: C=12.1 liter/cm$^2$-sec*D$^3$/L=4*10$^{-6}$ liter/sec.
A conservative estimate of the out-gassing rate is made and accordingly the out-gassing rate of the inner walls of the pumping tube is assumed to be: q=10$^{-12}$ Torr-liter/sec-cm$^2$.
It is assumed that the pressure at the pump inlet is P$_0$=10$^{-8}$ Torr.
Therefore, the pressure inside the x-ray transducer is:

$$P = P_0 + (qA)/(2C) = 8*10^{-5} \text{ Torr}$$

This result, 8*10$^{-5}$ Torr, is consistent with the demand for an operating pressure of 10$^{-4}$ Torr or better inside the transducer.
The required evacuated volume is 10 mm$^3$=10$^{-5}$ liter.
Therefore, the time it takes to pump-down the x-ray transducer is:

$$T = 10^{-5} \text{ liter}/4*10^{-6} \text{ liter/sec} = 2.5 \text{ sec}$$

As can be seen by the illustrated example, using of a dynamically pumped system is feasible and provides an effective mechanism for preserving the vacuum level in miniaturized energy transducers that emit x-rays. Furthermore, this mechanism removes stray gases regardless of their chemical reactivity, thus overcoming the problem of vacuum degradation due to non-absorbable gases. The embodiments described in accordance with the present invention do not require the introduction of getter material or vacuum sealing prior to the assembly of the x-ray transducer. Thus, the implementation of the dynamically pumped system makes the manufacturing of miniaturized x-ray transducers a relatively simple, inexpensive process. Additionally, the implementation of the dynamically pumped system enables the production of a relatively long shelf life device, as an appropriate vacuum level has to be maintained only during the operation of such a device.

The invention has been described with reference to certain preferred embodiments thereof. It will be understood, however, that modifications and variations are possible within the scope of the appended claims.

What is claimed is:

1. An elongated flexible insertion device comprising:
   an electrically conductive inner core;
   a dielectric material that surrounds the inner core;
   an outer shield that surrounds the dielectric material;
   an outer layer of electrical insulation that surrounds the outer shield; and
   a pumping conduit.

2. An elongated flexible insertion device as claimed in claim 1, wherein the maximum width of the cross section of the device is 2.4 mm.

3. An elongated flexible insertion device as claimed in claim 1, wherein the inner core is a hollow conduit that defines the pumping conduit.

4. An elongated flexible insertion device as claimed in claim 1, wherein the pumping conduit is embedded within the dielectric material.

5. An elongated flexible insertion device as claimed in claim 1, wherein the pumping conduit is coupled to the exterior of the outer shield.

6. An elongated flexible insertion device as claimed in claim 1, wherein the pumping conduit is embedded within the outer layer of electrical insulation.

7. An elongated flexible insertion device as claimed in claim 1, further comprising an optical conductor.

8. An elongated flexible insertion device as claimed in claim 1, wherein the inner core is a hollow conduit that defines the pumping conduit, and the optical conductor is housed within the pumping conduit.

9. An elongated flexible insertion device as claimed in claim 7, wherein the optical conductor is embedded within the inner core.

10. An elongated flexible insertion device as claimed in claim 7, wherein the pumping conduit is embedded within the dielectric material.

11. An elongated flexible insertion device as claimed in claim 7, wherein the pumping conduit is coupled to the exterior of the outer shield.

12. An elongated flexible insertion device as claimed in claim 7, wherein the pumping conduit is embedded within the outer layer of electrical insulation.

13. An x-ray emitting system comprising:
   an x-ray emitting energy transducer including a cavity that communicates with an evacuation opening therethrough;
   an external unit having a power supply, a vacuum pump, and a control unit; and
   an elongated flexible insertion device having a first end that is coupled to the external unit, a second end that is coupled to the x-ray emitting transducer, and including a pumping conduit that couples the evacuation opening of the x-ray emitting transducer to the vacuum pump, wherein a vaccum level is maintained within the cavity by evacuating the cavity with the vacuum pump.

14. An x-ray emitting system as clamed in claim 13, wherein:
the x-ray emitting energy transducer further comprises:
a transducer body having a first end and a second end;
a cathode structure provided at the second end of the transducer body; and
an anode structure provided at the first end end of the transducer body;
and the elongated flexible insertion device further comprises:
an electrically conductive inner core;
a dielectric material that surrounds the inner core;
an outer shield that surrounds the dielectric; and
an outer layer of electrical insulation that surround the outer shield.

15. An x-ray emitting system as clamed in claim 14, wherein
the cathode structure includes a cathode tube having a first end that protrudes into the interior of the transducer body and a second end that is coupled to second end of the transducer body, and a cathode that is coupled to the first end of the cathode tube, and
the anode structure includes an anode tube having a first end that protrudes into the interior of the transducer body and a second end that is coupled to the first end of the transducer body, and an anode that is coupled to the first end of the anode tube.

16. An x-ray emitting system as clamed in claim 15, wherein
the inner core is a hollow conduit that defines the pumping conduit, and
the evacuation opening extends through the anode tube.

17. An x-ray emitting system as claimed in claim 16, wherein
the elongated flexible insertion device further comprises an optical conductor that is housed within the pumping conduit,
the optical conductor extends through an opening in the anode, and
the evacuation opening extends through the anode tube.

18. An x-ray emitting system as claimed in claim 15, wherein
the pumping tube is embedded within the dielectric of the flexible insertion device, and the evacuation opening extends through the first end of the transducer body.

19. An x-ray emitting system as claimed in claim 15, wherein
the pumping tube is embedded within the dielectric of the flexible insertion device,
the evacuation opening extends through the transducer body,
the elongated flexible insertion further comprises an optical conductor that is embedded within the inner core, and
the optical conductor extends through an opening in the anode.

20. An x-ray emitting system as claimed in claim 15, wherein the pumping tube is embedded within the outer layer of electrical insulation.

21. An x-ray emitting system as claimed in claim 20, wherein the elongated flexible insertion device further comprises an optical conductor that is embedded within the inner core, and the optical conductor extends through an opening in the anode.

22. An in-situ radiation treatment method comprising:
positioning a miniature x-ray energy transducer at a treatment site;
evacuating the miniature x-ray transducer to achieve a desired vacuum level;
energizing the miniature x-ray energy transducer to achieve a predetermined radiation dosage, and
continuously evacuating the miniature x-ray transducer to maintain a desired vacuum level.

23. An in-situ radiation treatment method as claimed in claim 20, further comprising:
measuring the radiation dosage achieved at the treatment site with a dosimeter.

24. An in-situ radiation treatment method as claimed in claim 22, wherein the miniaturized x-ray energy transducer is energized with at least one of electrical energy or optical energy.

* * * * *